(12) United States Patent
Bathurst et al.

(10) Patent No.: US 10,962,463 B2
(45) Date of Patent: Mar. 30, 2021

(54) SYSTEM AND METHOD FOR MEASURING DISSOLVED METAL CONCENTRATIONS USING A CHEMOSENSOR FILM

(71) Applicants: Bruce Middleton Bathurst, Brookfield, WI (US); Paul Edward Henning, New Berlin, WI (US)

(72) Inventors: Bruce Middleton Bathurst, Brookfield, WI (US); Paul Edward Henning, New Berlin, WI (US)

(73) Assignee: Aquametals, LLC, Wauwatosa, WI (US)

( * ) Notice: Subject to any disclaimer, the term of this patent is extended or adjusted under 35 U.S.C. 154(b) by 0 days.

(21) Appl. No.: 16/440,730

(22) Filed: Jun. 13, 2019

(65) Prior Publication Data

US 2020/0393350 A1    Dec. 17, 2020

(51) Int. Cl.
*G01N 15/06* (2006.01)
*G01N 33/18* (2006.01)
*G01N 15/00* (2006.01)

(52) U.S. Cl.
CPC ......... *G01N 15/06* (2013.01); *G01N 33/1813* (2013.01); *G01N 33/1893* (2013.01); *G01N 2015/0053* (2013.01); *G01N 2015/0681* (2013.01); *G01N 2015/0693* (2013.01)

(58) Field of Classification Search
CPC ...................................................... G01N 15/06
USPC ........................................................ 356/327
See application file for complete search history.

(56) References Cited

U.S. PATENT DOCUMENTS

| | | | |
|---|---|---|---|
| 5,133,901 A * | 7/1992 | Peterson ................ | G01N 23/12 209/3.2 |
| 2003/0096275 A1 * | 5/2003 | Laing ................... | C12Q 1/6825 435/6.11 |
| 2006/0228256 A1 * | 10/2006 | McDevitt ........... | G01N 33/5432 422/82.05 |
| 2007/0037225 A1 * | 2/2007 | Metzger ............. | G01N 33/5438 435/7.22 |
| 2010/0195099 A1 * | 8/2010 | Rockney ................ | G01N 21/75 356/326 |
| 2019/0064062 A1 * | 2/2019 | Wang .................. | G01N 21/783 |

FOREIGN PATENT DOCUMENTS

WO    WO 2017/066672 A1    4/2017

* cited by examiner

*Primary Examiner* — Tarifur R Chowdhury
*Assistant Examiner* — Omar H Nixon
(74) *Attorney, Agent, or Firm* — Reinhart Boerner Van Deuren P.C.

(57) ABSTRACT

A system for analyzing a chemosensor that includes a light source directed at a chemosensor, and a spectrometer arranged to detect a signal from the light source after passing through the chemosensor. The spectrometer includes signal conditioning electronics and spectral decomposition software which allows the spectrometer to perform a spectral analysis in order to identify, in real time, one or more heavy metals in a continuous flow of water interacting with one or more dyes on the chemosensor.

20 Claims, 10 Drawing Sheets

SYSTEM AND METHOD FOR MEASURING DISSOLVED METAL CONCENTRATIONS USING A CHEMOSENSOR FILM

FIELD OF THE INVENTION

This invention generally relates to a system and method for measuring dissolved metal concentrations in liquids such as water using a chemosensor configured to detect the presence of dissolved metals.

BACKGROUND OF THE INVENTION

Real-time monitoring of environmental and industrial waters for metal pollutants of concern for public and environmental health via the standard methods of sampling followed by laboratory analysis is not possible or practical with current technology. Toxic metal ions enter environmental waters, through improperly treated industrial waste water, landfills, and mine runoff. Although many monitoring methods have been tried, there is no proven technology capable of reliably measuring low levels of pollutant concentrations in real time, in the field. There is a critical need for a real-time monitoring system to ensure and enforce regulatory compliance and to warn of threats to public and environmental health.

Embodiments of the invention provide such a real-time monitoring system and method of operating same. These and other advantages of the invention, as well as additional inventive features, will be apparent from the description of the invention provided herein.

BRIEF SUMMARY OF THE INVENTION

In one aspect, embodiments of the invention provide a system for measuring dissolved metal concentrations using a chemosensor that includes a light source directed at a chemosensor, and a spectrometer arranged to detect a signal from the light source after passing through the chemosensor. The spectrometer includes signal conditioning electronics and spectral decomposition software which allows the spectrometer to perform a spectral analysis in order to identify, in real time, one or more heavy metals in a flow of water interacting with one or more dyes on the chemosensor.

Some embodiments also include an aperture disposed between the light source and chemosensor, while other embodiments include a pump to facilitate a continuous flow of water across the chemosensor. Furthermore, the spectrometer may include a communications module to transmit spectral analysis data to a local or remotely located user interface device. In a particular embodiment, the user interface device is one of a smartphone, tablet computer, mobile computer, industrial human machine interface (HMI), a dedicated single-board computer interface, and desktop computer.

Particular embodiments of the invention include a source for a sensor regeneration reagent, wherein the sensor regeneration reagent removes all metals bound to the chemosensor. Other embodiments include a source for a sensor wash and baseline calibration reagent, referred to herein as the sensor recalibration reagent. The sensor recalibration reagent is configured to flush regeneration reagent out of the chemosensor. Once the recalibration reagent has flushed out all of the regeneration reagent, the chemosensor may be used to obtain a baseline spectrometer signature for differential spectrometer readings. Embodiments of the invention may also include a degassing unit to remove dissolved gases and air bubbles from the flow of water before interaction with the chemosensor.

An n-way selector valve may be positioned upstream of the chemosensor, the n-way selector valve configured to selectively supply any one or any combination of "n" liquids to the chemosensor, where "n" is a number equal to, or greater than, two. Embodiments of the invention may also include a mixer positioned between the n-way selector valve and the chemosensor.

The spectral analysis is able to identify the presence of one or more of iron, copper, cadmium, tin, silver, chromium, cobalt, lead, manganese, mercury, zinc, and nickel in the water flowing across the chemosensor. In a further embodiment, the spectral analysis is able to specify the concentration of one or more of iron, copper, cadmium, tin, silver, chromium, cobalt, lead, manganese, mercury, zinc, and nickel in the water flowing across the chemosensor.

In a further embodiment of the invention, the spectral decomposition software is configured to use a partial least squares model built from calibration data. In a more particular embodiment, the spectral decomposition software computes a time-averaged concentration of heavy metals in a flow of water based on a calculation of the accumulated metal within the chemosensor.

In another aspect, embodiments of the invention provide a method of measuring dissolved metal concentrations using a chemosensor. The method calls for providing a flow of water across the chemosensor which has one or more dyes each configured to change colors due to interaction with a specific group of metals. The method also includes directing light from a light source at the chemosensor while the flow of water is flowing across the chemosensor, and performing a spectral analysis of the light transmitted through the chemosensor. The method further includes determining, in real time based on the spectral analysis, a concentration of one or more metals dissolved in the flow of water.

The method may also include degassing the flow of water to remove dissolved gases and air bubbles before the flow of water interacts with the chemosensor, and may also include regenerating the chemosensor and recalibrating the spectral baseline prior to providing the flow of water across the chemosensor. Certain embodiments of the method include washing the chemosensor to flush out regeneration reagents prior to providing the flow of water with dissolved metals across the chemosensor. In a further embodiment, the method requires directing light through an aperture at the chemosensor.

In a particular embodiment, the method includes identifying one or more of iron, copper, cadmium, tin, silver, chromium, cobalt, lead, manganese, mercury, zinc, and nickel. The method may also call for pumping a flow of water across the chemosensor at a known flow rate. A more particular embodiment calls for transmitting spectral analysis data to a local or remotely located user interface device.

In certain embodiments, the method also includes using a partial least squares model built from calibration data to determine an amount of metal accumulation on the chemosensor based on data from the spectral analysis. Several metals may be uniquely identified using the data from one chemosensor. Additionally, the method may call for calculating a time-averaged concentration of heavy metals in a flow of water using a water flow rate, an elapsed time, and the amount of metal accumulation on the chemosensor.

In yet another aspect, embodiments of the invention provide a flow cell assembly for measuring dissolved metal concentrations using a chemosensor. The flow cell includes a body portion with a slotted opening into which a cartridge containing the chemosensor can be inserted and held in a fixed position. A channel opening is formed through the body portion. The channel opening is configured to provide a continuous flow of water to at least a portion of the chemosensor when the cartridge is fixed in the slotted opening. An optical opening is formed through the body portion. The optical opening has a first end on a first side of the body portion and a second end on a second side of the body portion opposite the first side. The optical opening is configured to provide a path for light from a light source to pass through the chemosensor when the cartridge is fixed in the slotted opening. The light source is attached to the body portion and located at the first end of the optical opening. A spectrometer is located at a fixed position outside of the second end of the optical opening. The spectrometer has signal conditioning electronics and spectral decomposition software which allows the spectrometer to perform a spectral analysis to identify, in real time, one or more heavy metals dissolved in a flow of water interacting with one or more dyes on the chemosensor.

In a particular embodiment, the channel opening is orthogonal to the optical opening. In a more particular embodiment, the channel opening and the optical opening intersect at some point along the slotted opening. In a further embodiment, the body portion is attached to one side of a bracket wall, the spectrometer is attached to the opposite side if the bracket wall, the bracket wall having an opening aligned with both the optical opening and an optical sensor of the spectrometer.

In yet another aspect, embodiments of the invention provide a system for measuring dissolved metal concentrations using a chemosensor. The system includes a plurality of the aforementioned flow cell assemblies connected in series. A flow line connects the channel openings of adjacent flow cell assemblies. The flow line is configured to provide a single continuous flow of water through each of the plurality of flow cell assemblies.

In certain embodiments, the system includes a pump connected to the flow line. The pump is configured to provide the single continuous flow of water through each of the plurality of flow cell assemblies at a controlled flow rate.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

Figure 1:
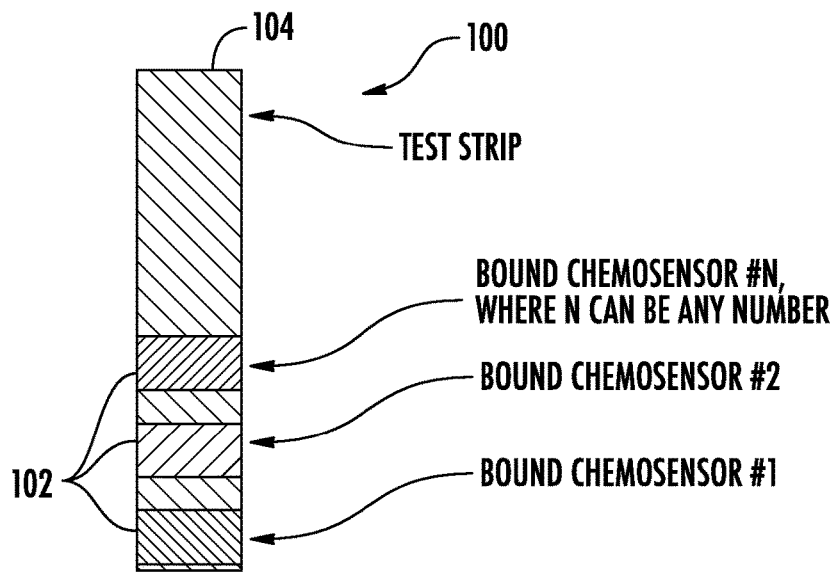
FIG. 1 show an exemplary embodiment of a chemosensor test strip of the type to be used with embodiments of the invention described herein.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Described hereinbelow are embodiments of systems and methods for the continuous analysis of flowing water or flowing liquids for the presence of one or more heavy metals. The system will be described below as determining a concentration of heavy metals within a flow of water. However, in the context of the present invention, the term "water" may indicate a solution or fluid mixture that includes elements or liquids other than water or in addition to water, which is likely to include some measure of one or more dissolved metals.

In an embodiment of the invention, a chemosensor analyzer measures and identifies the concentration of multiple heavy metals dissolved in flowing water. In certain embodiments, the chemosensor analyzer continuously measures the concentration of multiple heavy metals in real time by computing the rate at which dissolved metals in flowing water bind with optical dye sensors that include fluorescent or absorbance dyes that are, in turn, bound in a polymer matrix.

The aforementioned chemosensors are described in International Patent Publication No. WO 2017/066672 by UWM Research Foundation, Inc., filed on Oct. 14, 2016, the entire teachings and disclosure of which is incorporated herein by reference. More specifically, the UWM patent publication discloses a class of absorbance and fluorescent dyes permanently embedded in a polymer that changes spectral signatures when exposed to specific heavy metals.

An exemplary chemosensor changes optically in the presence of specific metal ions in aqueous or non-aqueous environments. There are chemosensors for metal ions in aqueous or non-aqueous environments that are sensitive to changes in metal ion concentration. Some chemosensors are reusable, repeatable so as to produce consistent measurements, and can be covalently attached to other materials. The binding of metal ions to the dye may mediate a change in the dye-generated signal. That is, when the metal ion is unbound, the dye generates a signal, and when metal ion is bound, the signal generated from the dye changes. The dye may bind one metal ion at a time. In some embodiments, the dye is able to bind multiple metal ions at the same time. In some embodiments, the dye generates unique spectral features for each bound metal ion.

Typically, the dye detects a metal ion over a linear dynamic range of about 1 ppb to about 10,000 ppb. However, the dye may also detect a metal ion over a linear dynamic range of at least about 50 ppb to at least 5,000 ppb. In some cases, the dye detects a metal ion over a linear dynamic range of less than about 1 ppb to less than about 1,000 ppb. In other cases, the dye detects a metal ion over a linear dynamic range of about 0.1 ng/mL to about 10,000 ng/mL, or any range in between.

The dye may be reusable for metal ion detection, that is, the dye may be used multiple times to detect the same or different metal ions. After being used to detect a metal ion, the dye may be treated with a weak electrolyte solution, a dilute acid solution, or a solution containing a chelating agent. An example of a dilute acid solution is 0.1 M hydrochloric acid. An example of a weak electrolyte solution includes, for example, water with a small amount of one or more salts, where the weak electrolyte solution acts to release the bound metals from the chemosensor.

In some embodiments, the signal is an optical signal. The change in the signal may be an increase or a decrease in the absorbance at a single wavelength or range of wavelengths. In various embodiments, the increase or decrease in the absorbance may range from about 0.001 differential absorbance units, to about 1.5 differential absorbance units. Generally, the signal indicates the absorbance of the dye recorded at a single wavelength or range of wavelengths at any moment in time. The change in the signal over time may be due to a shift in the single wavelength or range of wavelengths from about 1 nm to about 800 nm, or any range in between.

In other embodiments, the signal is fluorescence. The change in signal may be due to an increase or decrease in the fluorescence intensity of the dye. The increase or decrease in the fluorescence intensity may be within a range of about 1% to 100% of the chemosensor's maximal fluorescence, or any range in between.

FIG. 1 show an exemplary embodiment of a chemosensor test strip 100 of the type to be used with embodiments of the invention described herein. The test strip 100 is made up of one or more heavy metal chemosensors 102 bound to a substrate 104. The substrate 104 may be optically transparent to provide for sufficiently low light-scattering. In some cases, the optical density of the substrate 104 ranges from less than 0.001 to about 2.0 absorbance units, or any range in between, depending on the scattering signal relative to sensor signal. The substrate 104 may be fabricated from materials that include hydrophilic polymers, hydrophobic polymers, cellulose, or gels.

Immersing the test strip 100 in a solution of metals causes the test strips to change color, thereby allowing for the determination of information on the specific heavy metals present in the solution using spectral analysis.

Figure 2:
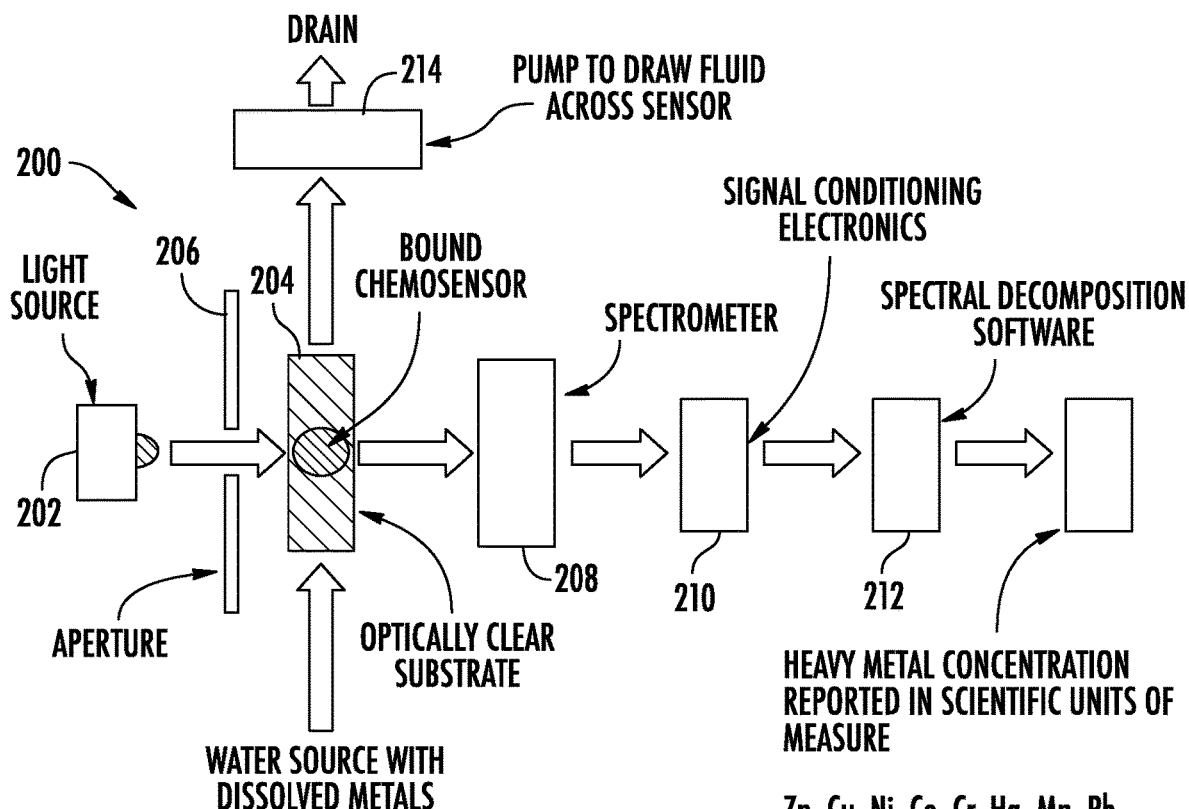
FIG. 2 is a schematic illustration of a system for measuring dissolved metal concentrations using a chemosensor, in accordance with an embodiment of the invention.

FIG. 2 is a schematic illustration of a system for analyzing a chemosensor 200, in accordance with an embodiment of the invention. The system includes a light source 202. In the embodiment of FIG. 2, light from the light source 202 is directed onto a chemosensor test strip 204 through an aperture 206. However, it is envisioned that there are embodiments of the system 200 which do not include an aperture 206. Light that has passed through the chemosensor 204 is captured by a spectrometer 208 that includes signal conditioning electronics 210 and spectral decomposition software 212. The signal conditioning electronics 210 and spectral decomposition software 212 process the light signal detected by the spectrometer 208 to determine a concentration of heavy metals in a flow of water across the chemosensor 204.

In operation, the system 200 is able to continuously measure the concentration of multiple metals in the flow of liquid until the chemosensor 204 saturates. When that happens, the chemosensor 204 is replaced. A source of water, which may include dissolved metals, supplies the flow across chemosensor 204. Typically, that water is then directed to a drain or reservoir of some kind for disposal. In particular embodiments, a pump 214 is used to help draw the water across the chemosensor 204. In other embodiments, the pump 214 is not needed.

The system 200 determines the amount of heavy metals in the stream of flowing water by using the spectrometer 208 to measure the absorbance of light through the chemosensor 204 while the sample water/liquid is flowing over it. In particular embodiments, a new spectral measurement, based on light absorbance through the chemosensor 204, is processed on a continuous basis (e.g., every 1 to 5 seconds), and changes in the spectra over time are used to calculate the concentration of one or more heavy metals at any given time. In certain embodiments, when the absorbance of the chemosensor 204 reaches an upper limit, the system 200 will stop drawing the flow of water through the chemosensor 204 and, in certain embodiments, will notify the user that the chemosensor 204 must be replaced.

Figure 3:
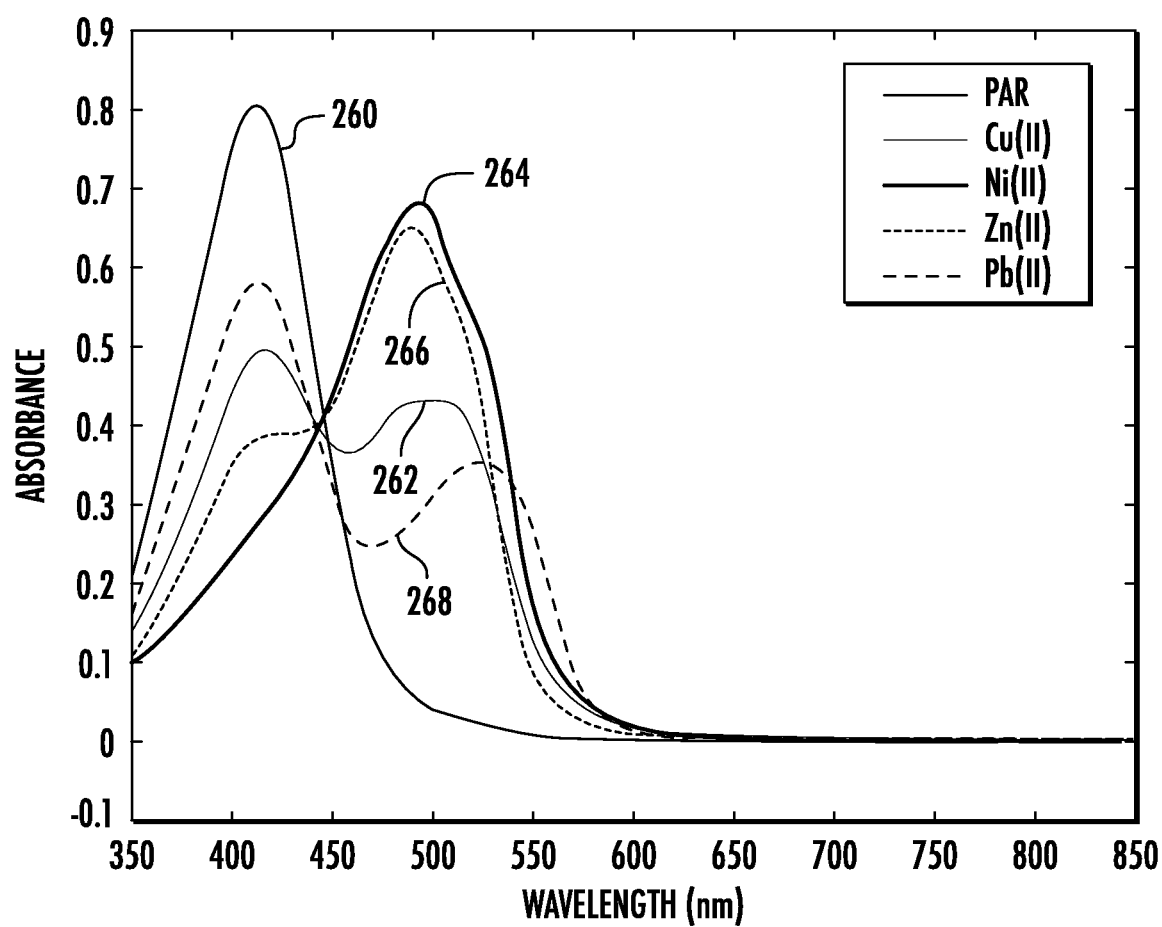
FIG. 3 is an exemplary graphical representation of the differential absorbance band spectra for copper, nickel, zinc, and lead.

Different metals produce different spectra (based on its differential absorbance band) when bound to a dye in a solution such that each metal can be identified by its unique spectral signature. FIG. 3 is an exemplary graphical representation of the differential absorbance band spectra for copper 262, nickel 264, zinc 266, and lead 268. In the graph of FIG. 3, there is also a spectrum 260 for PAR (4-(2-pyridylazo) rescorinol), which is the type of dye used on the chemosensor 204. The spectral decomposition software 212 is configured to recognize the various individual spectra for all of the heavy metals that can be detected by the chemosensor 204.

Figure 4:
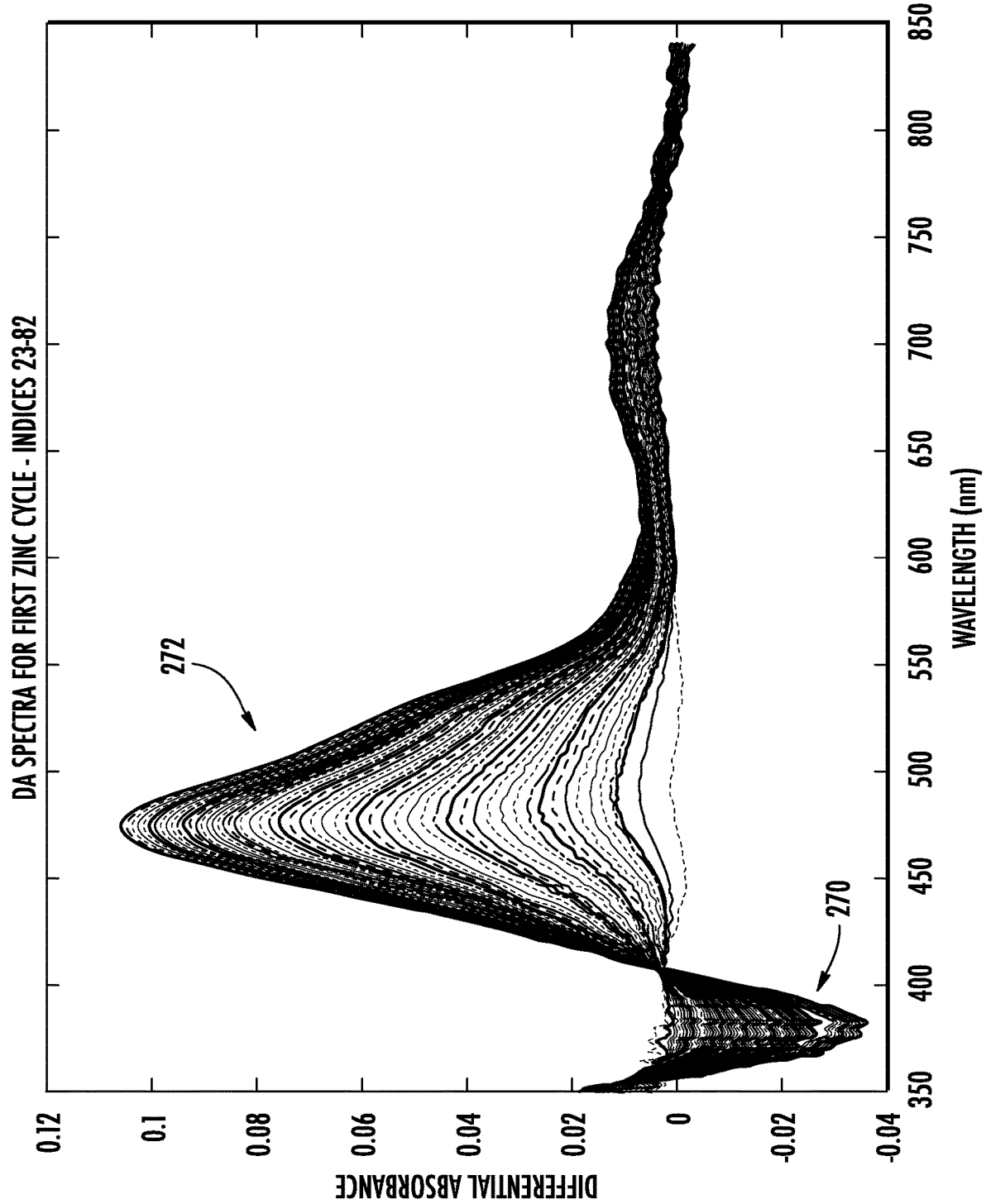
FIG. 4 is a graphical representation showing the growth of the spectral signal strength over time resulting from an increased accumulation of specific metals in the chemosensor.

During operation of the system 200 using a properly regenerated chemosensor 204, the chemosensor differential absorbance spectra increases in amplitude over time. The regeneration process is explained in more detail below. The increase in differential absorbance spectra amplitude is illustrated in the graphical representation of FIG. 4, which shows examples of differential absorbance bands 270, 272 over time for a water flow containing dissolved zinc. A negative band 270 is present in each differential absorbance scan. The differential absorbance bands 270, 272 increase or decrease over time as metal binds to the sensor molecules in the chemosensor 204. This behavior of the differential absorbance bands 270, 272 over time used by the spectral decomposition software 212 in the real-time determination of heavy metal concentration in a flow of water. Also, the behavior is repeatable after chemically removing metals via regeneration from the chemosensor 204 and then washing the chemosensor 204, as described below. This chemosensor 204 treatment allows for repeated real-time measurements of heavy metal concentration in a flow of water.

Heavy metal concentration is computed by the spectral decomposition software 212 based on the water flow rate, rate of metal accumulation in the sensor film, and elapsed time. We take the spectrum at any given non-zero time. We then put that spectral data into a partial least squares (PLS) model built from calibration data. The spectral decomposition software 212 uses the PLS model to output the amount of one or more accumulated metals. From there, the spectral decomposition software 212 can compute the time-averaged concentration of these heavy metals using the flow rate and elapsed time.

Figure 5:
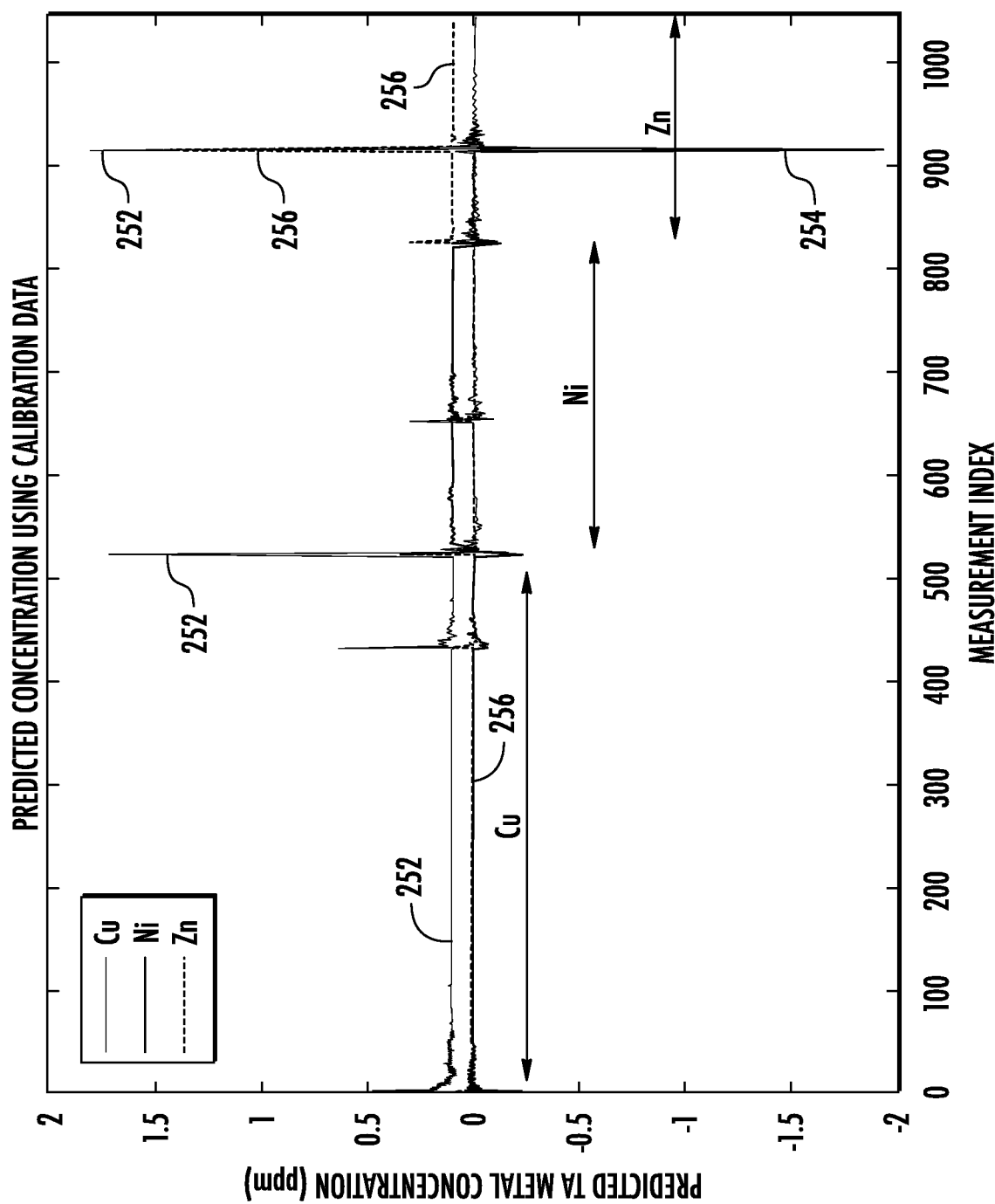
FIG. 5 is an exemplary graphical illustration showing the predicted time-averaged metal concentration of three different metals.

FIG. 5 is an exemplary graphical illustration showing the predicted time-averaged metal concentration of three different metals. In this example, the spectral decomposition software 212 establishes upper and lower bounds to distinguish copper 252, Nickel 254, and Zinc 256 spectra in the same solution of flowing water. Many other metals can also be differentiated using the partial least squares model.

Figure 6:
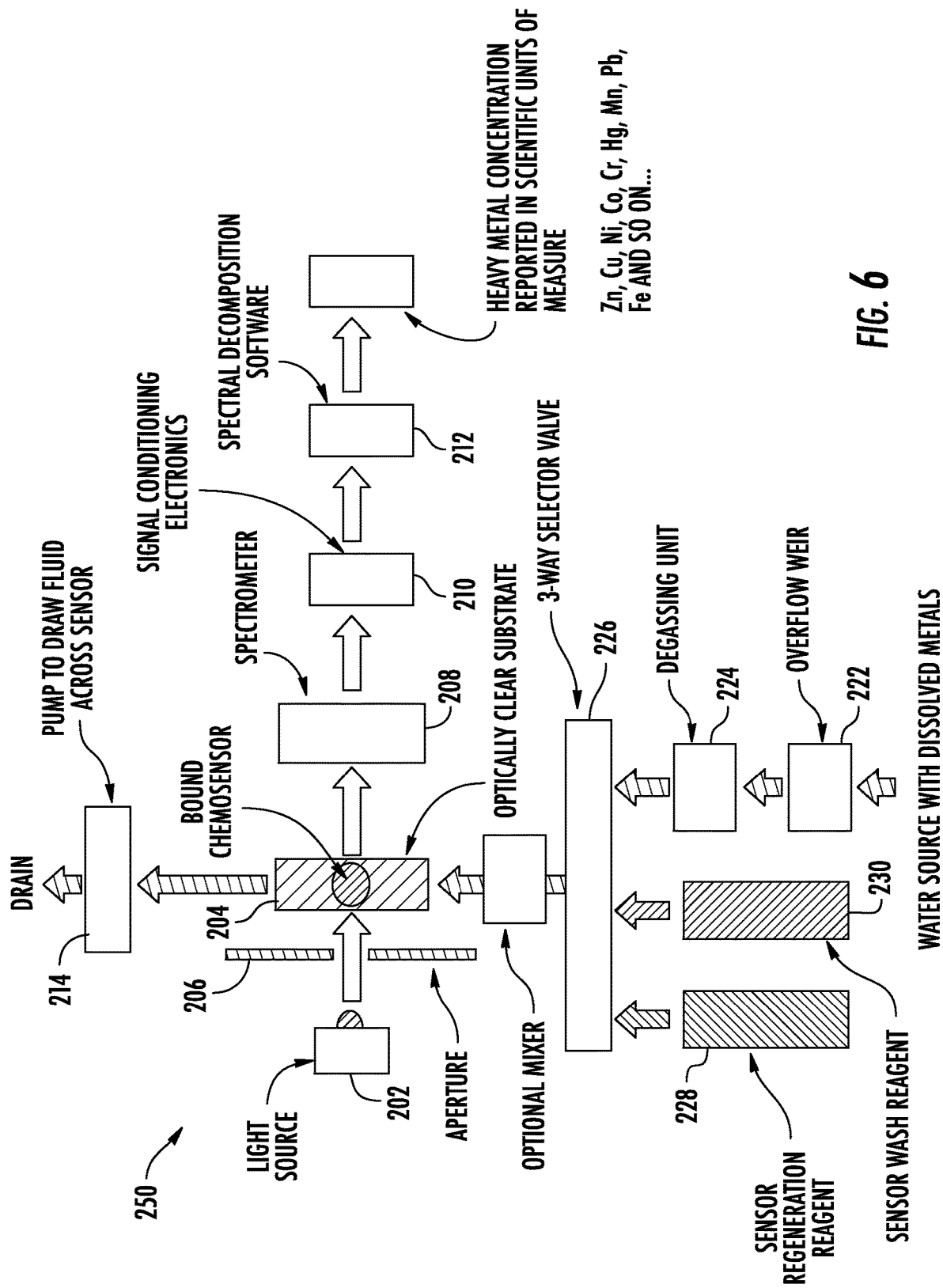
FIG. 6 is a schematic illustration of a system for measuring dissolved metal concentrations using a chemosensor, in accordance with a different embodiment of the invention than that shown in FIG. 2.

FIG. 6 is a schematic illustration of a system for analyzing a chemosensor 250, in accordance with a different embodiment of the invention than shown in FIG. 2. The embodiment of FIG. 6 includes the same light source 202, chemosensor 204, spectrometer 208, signal conditioning electronics 210, spectral decomposition software 212, and optional aperture 206 and pump 214. However, the embodiment of FIG. 6 further includes an overflow weir 222 to hold the water to be supplied to the chemosensor 204. The overflow weir 222 receives water from a source wherein the water may include dissolved metals.

In the embodiment of FIG. 6, the overflow weir 222 is coupled to a degassing unit 224 configured to remove dissolved gases from the water flowing from the overflow weir 222. Upon exiting the degassing unit 224, the water flows to an n-way selector valve 226. The n-way selector valve 226 is configured to selectively provide a flow of liquid from "n" possible sources. The n-way selector valve 226 may provide the flow of a single liquid or any combination of the "n" liquids, where "n" is a number equal to, or greater than, two. A source for sensor regeneration reagent 228 is coupled to the n-way selector valve 226, as is a source for sensor recalibration reagent 230. An optional mixer 232 may be positioned between the n-way selector valve 226 and the chemosensor 204.

In operation, when the absorbance of the chemosensor 204 reaches some pre-determined upper limit, the system 250 may be configured to automatically stop drawing water through the chemosensor 204 to allow for a periodic sensor regeneration and baseline calibration. The baseline calibration is done by measuring the absorbance of light through the chemosensor 204 while the sensor recalibration reagent 230 is flowing over it. To commence regeneration of the chemosensor 204, the n-way selector valve 226 is arranged to allow a flow from the source for sensor regeneration reagent 228, while blocking any flow from the source for sensor recalibration reagent 230, and from the overflow weir 222 and degassing unit 224. The sensor regeneration reagent is made to remove all of the metals that may be bound to the chemosensor 204.

When the chemosensor 204 is properly regenerated and properly loaded with the correct amount of metal-detecting dye, there is a linear correlation between the concentrations of specific metals in flowing water to the increase in absorbance. Because the chemosensor 204 is configured to exhibit a highly linear spectral response to one or more metal ions over an extended time period, this enables the implementation of a partial least squares (PLS) model for the deployment of a predictive model such as that employed by the spectral decomposition software 212.

Additionally, the PLS model facilitates spectral differentiation such that each metal ion, when bonded to the dye, generates a semi-unique spectral response from the sensor. This feature enables the use of non-specific sensors (i.e., chemosensors 204 that bind and respond to more than one type of metal ion). Effectively, PLS allows for a model that takes advantage of the unique spectral components of the chemosensor 204 response to each metal ion.

Using the technique described above, it can be seen that the system 200 provides for the determination that the rate of specific metal accumulation is directly proportional to the concentration of metal flowing over the film at a constant rate. Furthermore, using the process described herein, these chemosensor 204-based measurements are repeatable and accurate.

Following regeneration, the chemosensor 204 is then washed with a sensor recalibration reagent 230 to flush out all acid and to run a baseline calibration of the measurement spectrum. To facilitate the wash, the n-way selector valve 226 allows a flow from the source for sensor recalibration reagent 230, while blocking any flow from the source for sensor regeneration reagent 228 and from the overflow weir 222 and degassing unit 224.

Following the wash, water may be drawn from the overflow weir 222 and supplied to chemosensor 204 at a fixed rate, though it is possible, in some embodiments, that the rate of flow may be variable. The optional pump 214 may be used to control the rate of flow of water from the overflow weir 222. Thus, the n-way selector valve 226 allows a flow of water from the overflow weir 222 and degassing unit 224, while blocking any flow from the source for sensor regeneration reagent 228 and the source for sensor recalibration reagent 230. The degassing unit 224 removes dissolved gasses from the water flowing from the overflow weir 222.

As described above with respect to the system 200 of FIG. 2, light passing through the chemosensor 204 is captured by the spectrometer 208 such that the signal conditioning electronics 210 and spectral decomposition software 212 process the light signal detected by the spectrometer 208 to determine a concentration of one or more heavy metals in the flow of water across the chemosensor 204.

Depending on the chemosensor 204 used, the spectral analysis may detect one or more of heavy metals that may include, but are not limited to, zinc, copper, cadmium, tin, silver, iron, lead, nickel, mercury, manganese, chromium, and cobalt. In certain embodiments, a new spectral measurement is processed on a continuous basis (every 1 to 5 seconds) and changes in spectra over time are used to calculate the concentration of multiple heavy metals at any given time. The results of the spectral analysis can be reported in real time to a local or remotely-located user interface. In this case, the user interface may be a desktop or mobile computer, an industrial human machine interface (HMI), a dedicated single-board computer interface, a tablet computer, smartphone, or some other suitable communications terminal that allows for the electronic receipt and display of information.

Figure 7:
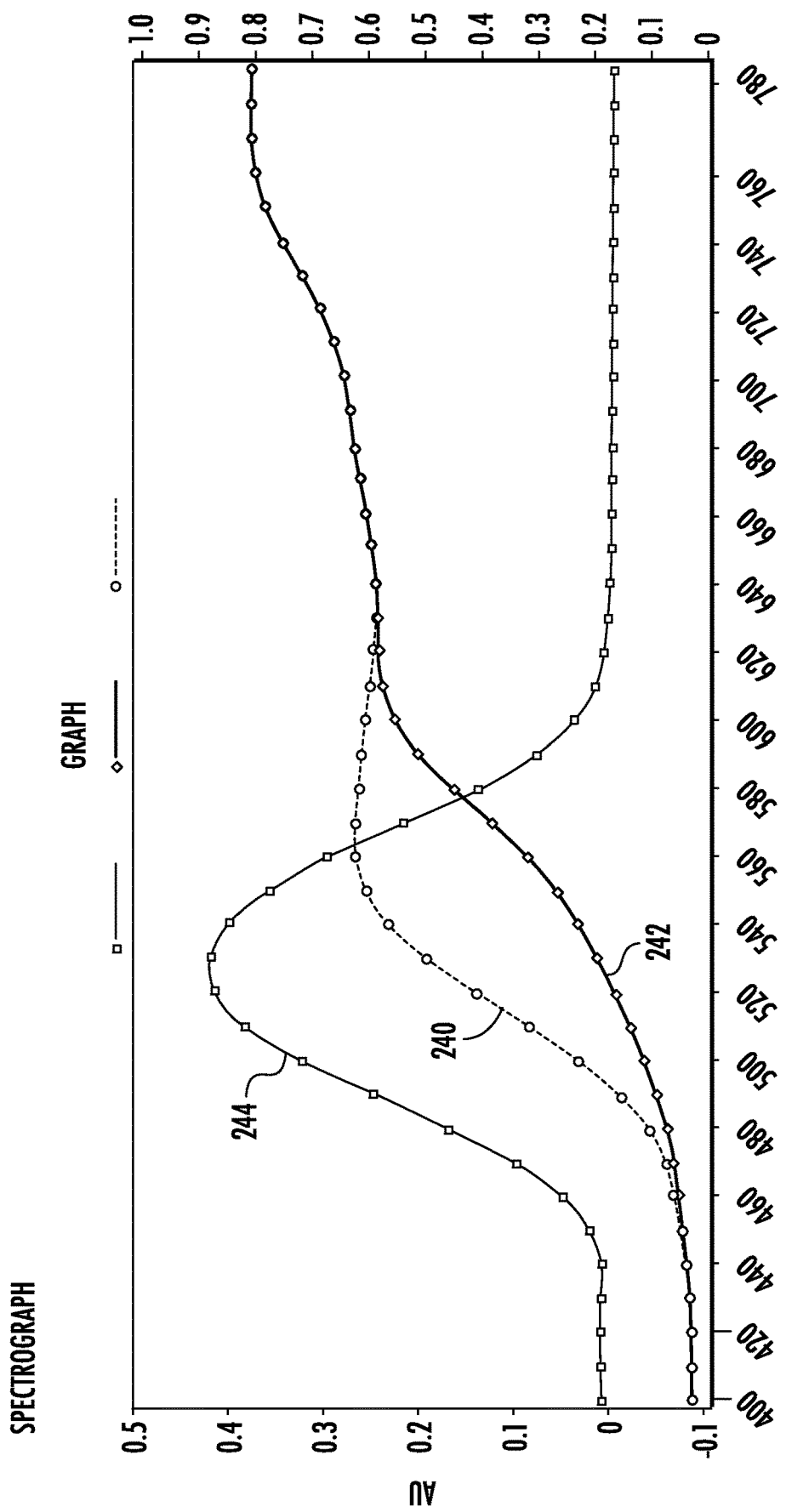
FIG. 7 is a graphical representation showing a spectral analysis with baseline calibration and peak differential absorbance for an exemplary water flow sample.

FIG. 7 is a graphical representation showing a spectral analysis with baseline calibration and peak differential absorbance for an exemplary water flow sample. Using the procedure described above, the system 250 initiates a baseline calibration of the chemosensor 204. The graph of FIG. 7 includes a first curve 240 showing a baseline spectrum, i.e., the lamp intensity transmitted through a regenerated chemosensor 204, as measured by the spectrometer 208. A second curve 242 shows lamp intensity transmitted through the chemosensor 204 following a spectral change caused by the bonding of the chemosensor 204 with a metal.

Once the baseline is established, any heavy metals in the water flow of interest are identified in curve 242 within the range of wavelengths from 400 nanometers (nm) to 800 nm and with respect to the differential absorbance vs. time. A third curve 244 shows the differential absorbance of the chemosensor 204 (bound to a metal) calculated from the two other curves 240, 242. The graph of FIG. 7 shows the chemosensor 204 with bound metal having a peak differential absorbance of 0.43 absorbance units (AU) at 525 nm. The rate at which the spectra grows as water flows over the sensor is used to identify specific concentrations of metals. The shape of the spectra identifies the specific metals present.

The chemosensor 204 may be assembled into a cartridge (as will be described below) to facilitate ease of handling and use. For example, a particular chemosensor 204 may include one or more dye sensors, sensitive to dissolved metals, covalently attached to a polymer matrix bound covalently to glass. This glass, polymer, chemosensor matrix, sometimes referred to as a sensor film, makes up the chemosensor 204. The chemosensor 204 is typically made to be optically thin and flat to obtain simple incident light characteristics. The chemosensor 204 may be glued into a carrier to form the aforementioned cartridge that is, in turn, inserted and sealed into a flow cell, as explained below.

Figure 8A:
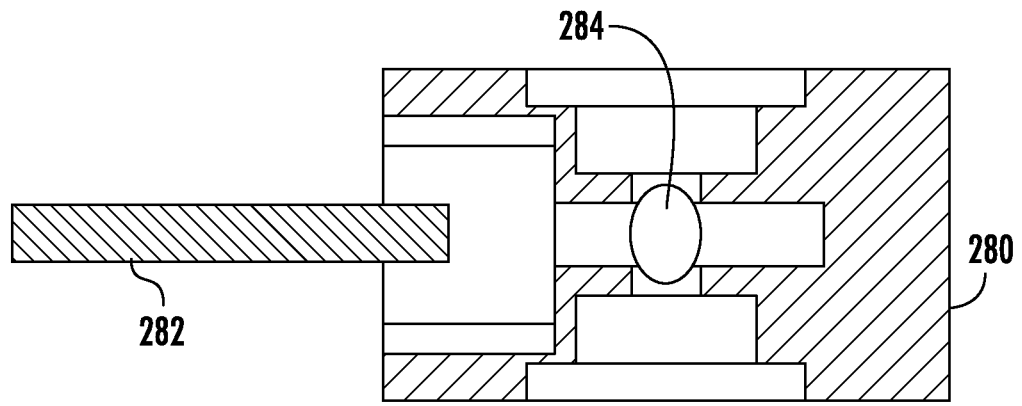
FIGS. 8A and 8B are schematic illustrations of a flow cell and chemosensor cartridge, in accordance with an embodiment of the invention.
Figure 8B:
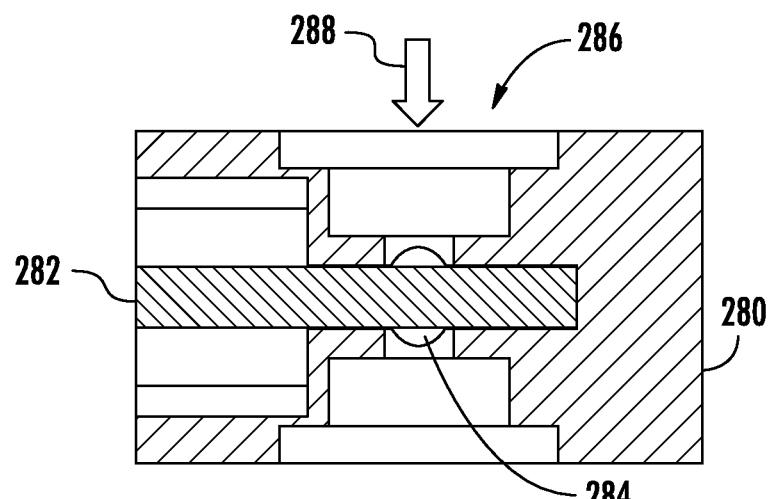

FIGS. 8A and 8B are schematic cross-sectional illustrations of a flow cell 280 and chemosensor cartridge 282, in accordance with an embodiment of the invention. The cartridge 282 is inserted into the flow cell 280 as shown in FIG. 8A. The cartridge 282 is seated and sealed into the flow cell 280, as shown in FIG. 8B. The flow cell 280 includes a channel 284 through which water flows into and out of the flow cell 280. In the context of FIGS. 8A and 8B, the water flows into the page past the dye sensor in the cartridge 282. While the water flows through channel 284 past the chemosensor 204, light is directed through an opening 286 along the path shown by arrow 288. The light enters the flow cell 280 through the opening 286 on one side of the flow cell 280, passes through the dye sensor on the chemosensor 204 in cartridge 282, exits through the opening 286 on the other side of the flow cell 280, and is detected by an optical sensor (not shown) for a spectrometer 354 (shown in FIG. 10). The optical sensor is positioned proximate the opening 286 on the side of the flow cell 280 where the light exits.

Figure 9:
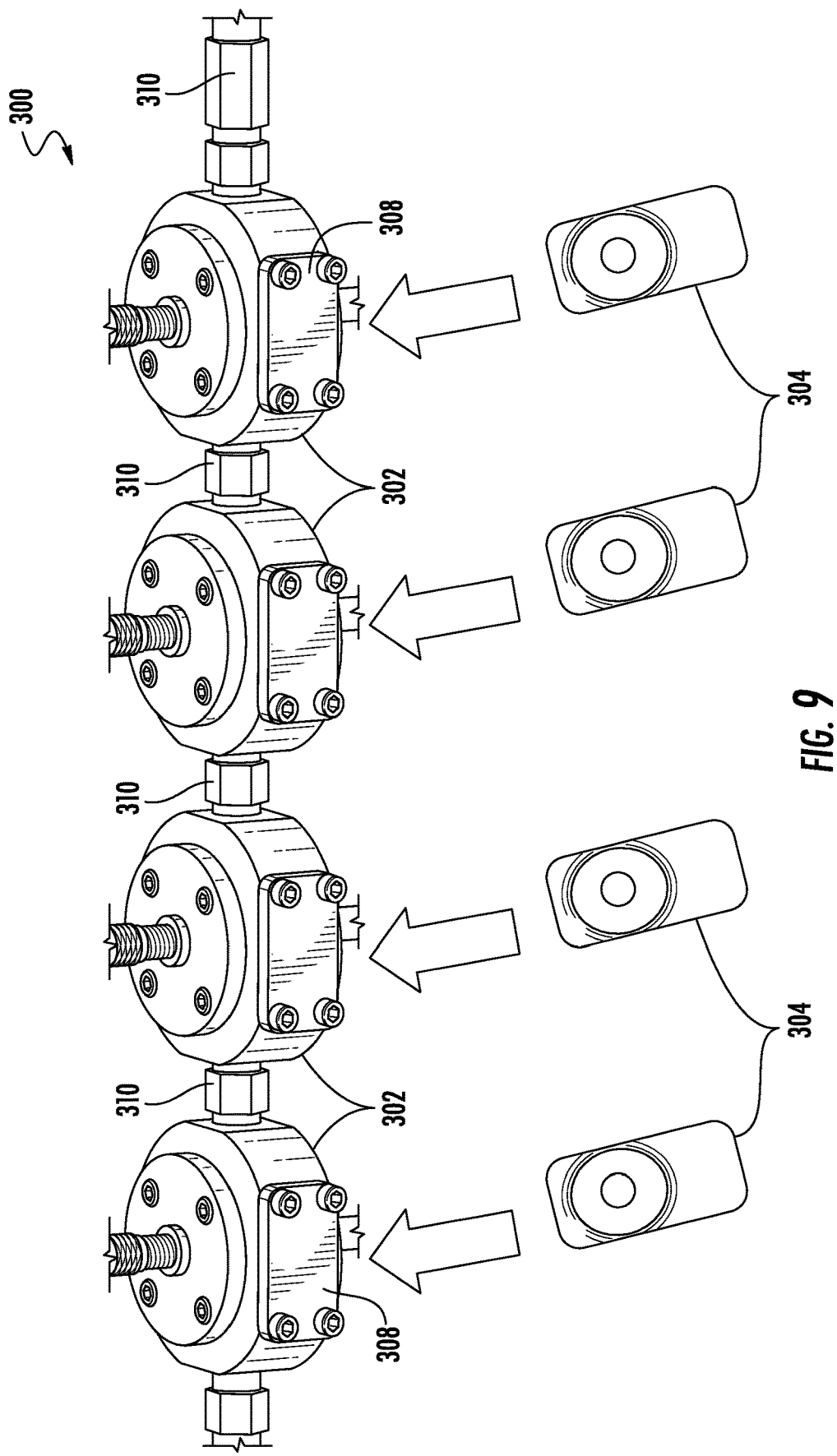
FIG. 9 is a perspective view of a system for measuring dissolved metal concentrations using a chemosensor where the system has four flow cells connected in series, constructed in accordance with an embodiment of the invention.

FIG. 9 is a perspective view of a system 300 for measuring dissolved metal concentrations using the chemosensor 204 where the system 300 has four flow cells 302 connected in series, in accordance with an embodiment of the invention. Alternate embodiments of the invention may have fewer or greater than four series-connected flow cells 302. The four flow cells 302 are connected in series to provide a consistent measurement by each of chemosensors 204. Each flow cell 302 may contain a cartridge 304 with a chemosensor 204 designed to detect a different group of metals. Since the flow rate of the process fluid over the chemosensors 204 is necessary for measurement accuracy, a series fluid flow arrangement guarantees that all chemosensors 204 in the four-unit assembly will have the same fluid flow rate. As such, the system 300 can be configured to detect four times the number of metals which could be detected by the systems of FIGS. 2 and 6, which show only one flow cell. Optical sensors 304 are shown to one side of each of the four flow cells 302. The sensor cartridges 304 are inserted and sealed under the plate 308. The embodiment of FIG. 9 show the plates 308 attached to the flow cells 302 with four screws. However, other suitable methods of attachment may be employed.

Water enters the system 300 via flow line 310 at one end of the system 300 and exits via flow line 310 at the other end.

In certain embodiments, a pump (not shown in FIG. 9) may be used to draw water through the system 300 at a known flow rate. In some embodiments, the light source may be remotely located such that the light directed at the chemosensor 204 is carried to the flow cells 302 by optical fibers. In alternate embodiments, the light source may be integrated into the flow cell 302 itself to reduce manufacturing cost and eliminate the need for fiber optics. Such an embodiment is described below in FIGS. 10 and 11.

Figure 10:
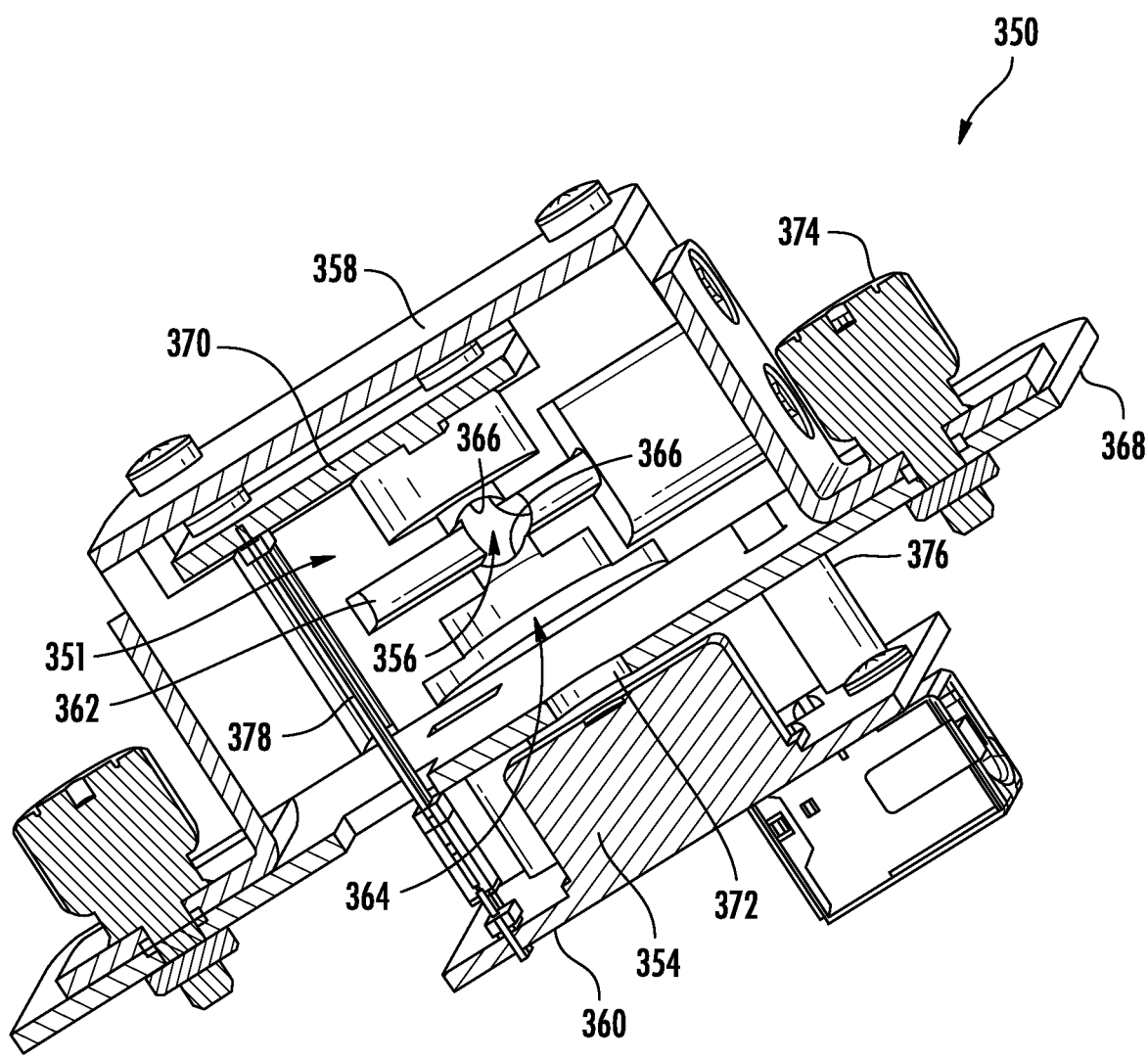
FIG. 10 is a cross-sectional view of a flow cell constructed in accordance with an alternate embodiment of the invention.
Figure 11:
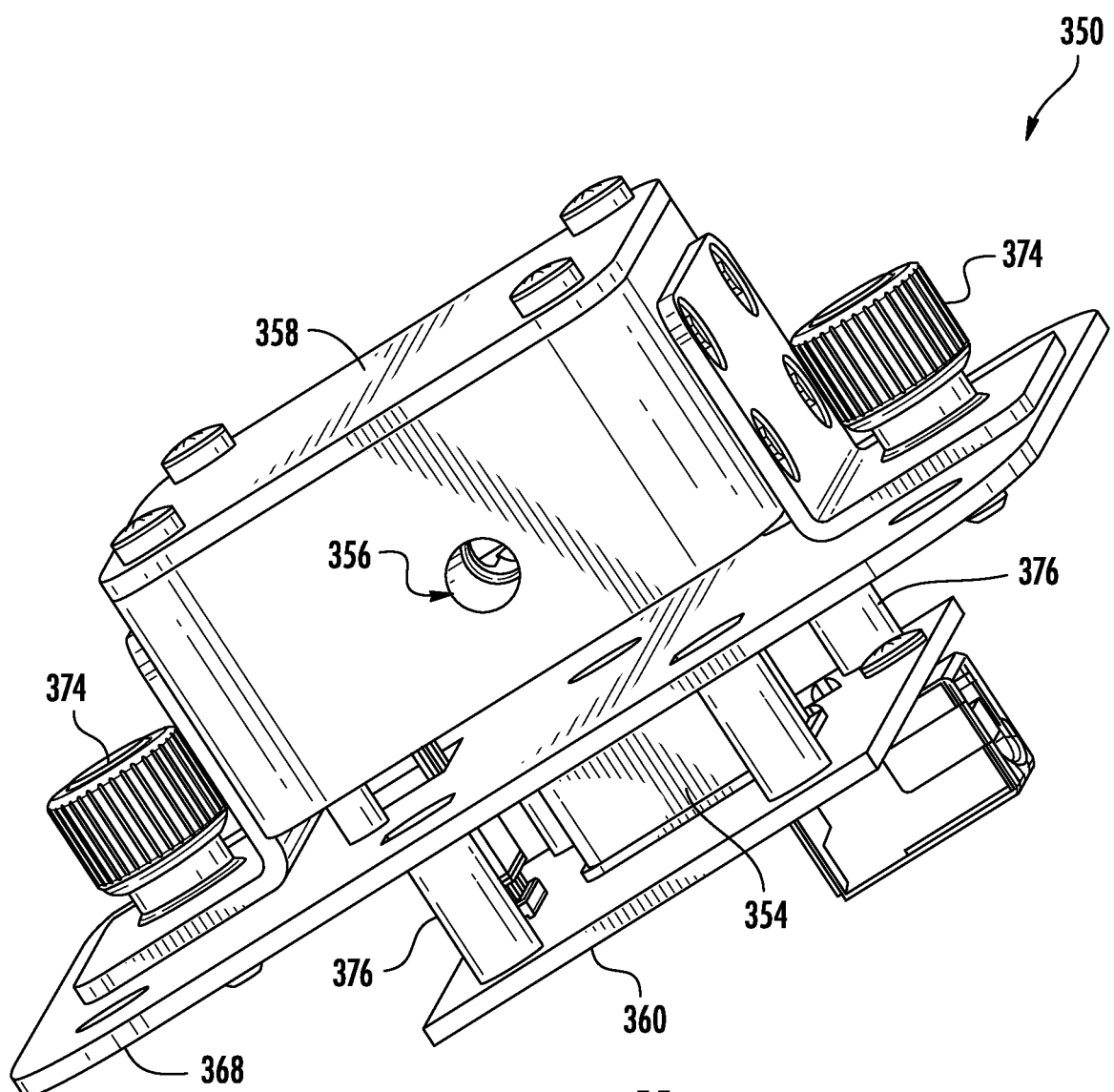
FIG. 11 is a perspective view of the flow cell of FIG. 10.

FIGS. 10 and 11 are cross-sectional and perspective views, respectively, of a flow cell assembly 350 constructed in accordance with an alternate embodiment of the invention. In certain embodiments of the invention, the flow cell assembly 350 is mounted to an electronics enclosure to close couple it to the spectrometer 354. The flow cell assembly 350 includes a body portion 351 with channel opening 356, sensor cartridge pocket 362, and optical opening 364. Water can be provided, at a known flow rate, to the chemosensor 204 (e.g., while housed in a cartridge) via channel opening 356 in the body portion 351.

A first printed circuit board 360 containing a spectrometer, with signal conditioning electronics and spectral decomposition software, along with circuitry data acquisition and communications circuitry is located outside of, but in relatively close proximity to, the body portion 351.

A second printed circuit board 370, containing a light source and electronic memory to hold calibration data, is attached to the body portion 351 and covered by a plate 358. The flow cell assembly 350 further includes a sensor cartridge pocket 362 which, in the embodiment shown, is a slotted opening in the body portion 351 into which the sensor cartridge 282 (shown in FIG. 8B) is inserted and sealed. As water flows through the channel opening 356 and across the chemosensor 204 in the sensor cartridge pocket 362, light from the light source on the second printed circuit board 370 is directed through optical opening 364, and through two apertures 366 on each side of the sensor cartridge pocket 362.

In the embodiment shown, the body portion 351 and the first printed circuit board 360 are attached to opposite sides of the same bracket wall 368. The bracket wall 368 has an opening 372 so that the spectrometer located on the first printed circuit board 360 receives light directed through the optical opening 364. In the embodiments shown, the body portion 351 is attached to one side of the bracket wall 368 using L-shaped brackets and thumb screws 374, and the first printed circuit board 360 is attached to the opposite side of the bracket wall 368 using standoffs 376. It should be noted that one of the L-shaped brackets covers the opening in the body portion 351 for the sensor cartridge pocket 362. Power is provided to the first and second printed circuit boards 360, 370 via connection 378. It is envisioned that power to the flow cell assembly 350 may be provided externally or internally, e.g., via battery.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for measuring dissolved metal concentrations using a chemosensor, the system comprising:
   a light source; and
   a spectrometer arranged to detect light from the light source after the light passes through the chemosensor;
   wherein the spectrometer includes signal conditioning electronics and spectral decomposition software which allows the spectrometer to perform a spectral analysis to identify, in real time, one or more heavy metals dissolved in a continuous flow of water interacting with one or more dyes on the chemosensor
   wherein the spectral decomposition software is configured to use a partial least squares model built from calibration data; and
   wherein the spectral decomposition software computes a time-averaged concentration of heavy metals in a flow of water based on a calculation of the accumulated metal on the chemosensor.

2. The system of claim 1, further including an aperture disposed between the light source and chemosensor.

3. The system of claim 1, further including a pump to facilitate the continuous flow of water across the chemosensor at a controlled flow rate.

4. The system of claim 1, wherein the spectrometer includes communications circuitry to transmit spectral analysis data to a local or remotely located user interface device.

5. The system of claim 4, wherein the user interface device is one of a smartphone, tablet computer, mobile computer, industrial human machine interface (HMI) a dedicated single-board computer interface, and desktop computer.

6. The system of claim 1, further including a source for a sensor regeneration reagent, wherein the sensor regeneration reagent removes all metals bound to the chemosensor.

7. The system of claim 1, further including a source for a sensor recalibration reagent, wherein the sensor recalibration reagent is configured to flush regenerating reagent out of the chemosensor and to facilitate a baseline spectral calibration of the chemosensor.

8. The system of claim 1, further including a degassing unit to remove dissolved gases from the flow of water before interaction with the chemosensor.

9. The system of claim 1, further including an n-way selector valve positioned upstream of the chemosensor, the n-way selector valve configured to selectively supply any one or any combination of "n" liquids to the chemosensor, where "n" is a number greater equal to, or greater than, two.

10. The system of claim 9, further including a mixer positioned between the n-way selector valve and the chemosensor.

11. The system of claim 1, wherein the spectral analysis is able to identify the presence of one or more of iron, copper, cadmium, tin, silver, chromium, cobalt, lead, manganese, mercury, zinc, and nickel in the water flowing across the chemosensor.

12. The system of claim 1, wherein the spectral analysis is able to specify the concentration of one or more of iron, copper, cadmium, tin, silver, chromium, cobalt, lead, manganese, mercury, zinc, and nickel in the water flowing across the chemosensor.

13. A method of measuring dissolved metal concentrations using a chemosensor comprising the steps of:
   providing a flow of water across the chemosensor which has one or more dyes each configured to change colors due to interaction with a specific type of metal;
   directing light from a light source at the chemosensor while the flow of water is flowing across the chemosensor;
   performing a spectral analysis of the light passing through the chemosensor;
   determining, in real time based on the spectral analysis, a concentration of one or more metals dissolved in the flow of water;
   using a partial least squares model built from calibration data to determine an amount of metal accumulation on the chemosensor based on data from the spectral analysis; and
   calculating a time-averaged concentration of heavy metals in a flow of water using a water flow rate, an elapsed time, and the amount of metal accumulation on the chemosensor.

14. The method of claim 13, further comprising the step of degassing the flow of water to remove dissolved gases before the flow of water interacts with the chemosensor.

15. The method of claim 13, further comprising the step of regenerating the chemosensor prior to providing the flow of water across the chemosensor.

16. The method of claim 13, further comprising the step of washing the chemosensor to flush out acids prior to providing the flow of water across the chemosensor.

17. The method of claim 13, wherein directing light from a light source at the chemosensor comprises directing light through an aperture at the chemosensor.

18. The method of claim 13, wherein identifying in real time one or more metals dissolved in the flow of water comprises identifying one or more of iron, copper, cadmium, tin, silver, chromium, cobalt, lead, manganese, mercury zinc, and nickel.

19. The method of claim 13, further comprising transmitting spectral analysis data to a local or remotely located user interface device.

20. The method of claim 13, wherein providing a flow of water across the chemosensor comprises pumping a flow of water across the chemosensor at a known flow rate.

* * * * *